US012733831B2

(12) United States Patent
Yu et al.

(10) Patent No.: US 12,733,831 B2
(45) Date of Patent: Sep. 15, 2026

(54) METHOD AND SYSTEM FOR EXTRACTING TARGET SIGNAL BASED ON MAXIMUM CORRELATED KURTOSIS DECONVOLUTION

(71) Applicant: Institute of Medical Support Technology, ISE, AMS, Tianjin (CN)

(72) Inventors: Ming Yu, Tianjin (CN); Qinwei Li, Tianjin (CN); Feng Chen, Tianjin (CN); Hang Wu, Tianjin (CN); Guang Zhang, Tianjin (CN)

(73) Assignee: Institute of Medial Support Technology, ISE, AMS, Tianjin (CN)

( * ) Notice: Subject to any disclaimer, the term of this patent is extended or adjusted under 35 U.S.C. 154(b) by 553 days.

(21) Appl. No.: 18/360,400

(22) Filed: Jul. 27, 2023

(65) Prior Publication Data

US 2025/0031988 A1 Jan. 30, 2025

(51) Int. Cl.

| | |
|---|---|
| ***A61B 5/0507*** | (2021.01) |
| ***A61B 5/00*** | (2006.01) |
| ***A61B 5/02*** | (2006.01) |
| ***G06T 12/20*** | (2026.01) |

(52) U.S. Cl.

CPC .......... *A61B 5/0507* (2013.01); *A61B 5/0042* (2013.01); *A61B 5/02042* (2013.01); *A61B 5/7203* (2013.01); *A61B 5/7246* (2013.01); *A61B 5/725* (2013.01); *A61B 5/7257* (2013.01); *G06T 12/20* (2026.01); *A61B 2562/0228* (2013.01); *A61B 2562/164* (2013.01); *A61B 2562/166* (2013.01); *A61B 2576/026* (2013.01)

(58) Field of Classification Search

CPC . A61B 5/0507; A61B 5/0042; A61B 5/02042; A61B 5/7203; A61B 5/7246; A61B 5/725; A61B 5/7257; A61B 2562/0228; A61B 2562/164; A61B 2562/166; A61B 2576/026; G06T 12/20; G16H 30/40

See application file for complete search history.

(56) References Cited

FOREIGN PATENT DOCUMENTS

| | | | | |
|---|---|---|---|---|
| CN | 114124038 A | * | 3/2022 | .......... G01M 13/045 |
| CN | 116361632 A | * | 6/2023 | ........... G06F 18/213 |

OTHER PUBLICATIONS

English machine translation of Zhao et al. (CN116361632A) (Year: 2023).*

(Continued)

*Primary Examiner* — Walter L Lindsay, Jr.
*Assistant Examiner* — Geoffrey T Evans
(74) *Attorney, Agent, or Firm* — Flener IP & Business Law

(57) ABSTRACT

A method and system for extracting a target signal based on maximum correlated kurtosis deconvolution are provided, which relate to a field of signal processing. The method includes: obtaining a microwave signal of a brain of a subject to be tested; filtering the microwave signal by using maximum correlated kurtosis deconvolution to obtain a filtered signal; performing mode decomposition on the filtered signal by using a complete ensemble empirical mode decomposition with adaptive noise to obtain a target response signal; and performing image reconstruction on the target response signal by using a delay sum beamforming to obtain a target bleeding image.

9 Claims, 12 Drawing Sheets

S1 — Obtaining a microwave signal of a brain of a subject to be tested

S2 — Filtering the microwave signal by using the MCKD to obtain a filtered signal S3 — Performing mode decomposition on the filtered signal by using a complete ensemble empirical mode decomposition with adaptive noise (CEEMDAN) to obtain a target response signal S4 — Performing image reconstruction on the target response signal by using a delay sum beamforming to obtain a target bleeding image

(56) References Cited

OTHER PUBLICATIONS

English machine translation of Li et al. (CN114124038A) (Year: 2022).*

"A Portable Microwave Intracranial Hemorrhage Imaging System Based on PSO-MCKD-CEEMDAN" by Li et al.; IEEE Transactions on Microwave Theory and Techniques; vol. 71, No. 2 (Year: 2023).*

* cited by examiner

METHOD AND SYSTEM FOR EXTRACTING TARGET SIGNAL BASED ON MAXIMUM CORRELATED KURTOSIS DECONVOLUTION

TECHNICAL FIELD

The present disclosure relates to a field of signal processing, and in particular, to a method and system for extracting a target signal based on maximum correlated kurtosis deconvolution.

BACKGROUND

Cerebral stroke is an acute cerebrovascular disease with high morbidity, mortality and disability rate, and includes hemorrhagic stroke and ischemic stroke respectively caused by cerebrovascular burst and cerebrovascular blockage. The effectiveness of treatment for the stroke depends on intervention time, and a patient's condition may deteriorate rapidly. Therefore a low-cost portable device for accurately monitoring the stroke is required to detect and identify the stroke and locations of bleeding points as early as possible, so as to provide more possibilities for saving more lives. Microwave detection began in the 1950s. With the rapid development of computer technology and electrical and electronic technology, coupled with the demand for practical applications, microwave signals have been used for detection and imaging in various directions such as agricultural and forestry and marine survey, military reconnaissance, mapping and charting, and wireless communications. Microwave signals have been extensively concerned in medical detection for their advantages of carrying large amount of information and high security.

Due to the complexity of human tissues, microwave will scatter when it penetrates the human body, which causes great difficulties in signal extraction and processing in the later stage. With the continuous improvement of antenna technology, microwave sensors and computer processing capabilities in recent years, the application of microwave in the medical field, especially in the detection for stroke, has been greatly promoted. As the advantages of microwave monitoring have been highlighted in various aspects, such as the cost of money, false drop rate, detection time and equipment size, the application of microwave imaging technology in medical monitoring has become an inevitable trend in the future. Therefore, how to apply microwave detection to stroke in the field of medical monitoring to improve a speed of acquiring the target signal for cerebral hemorrhage is a technical problem required to be solved urgently.

SUMMARY

An objective of the present disclosure is to provide a method and system for extracting a target signal based on maximum correlated kurtosis deconvolution (MCKD), to improve a speed of extracting a target signal for cerebral hemorrhage.

To achieve the above objective, the present disclosure provides the following technical solution.

A method for extracting a target signal based on the maximum correlated kurtosis deconvolution (MCKD) includes:

obtaining a microwave signal of a brain of a subject to be tested;

filtering the microwave signal by using the MCKD to obtain a filtered signal;

performing mode decomposition on the filtered signal by using a complete ensemble empirical mode decomposition with adaptive noise (CEEMDAN) to obtain a target response signal; and performing image reconstruction on the target response signal by using a delay sum beamforming to obtain a target bleeding image.

In an embodiment, obtaining the microwave signal of the brain of the subject to be tested may include:

arranging a plurality of antenna pairs along circumference of the brain of the subject to be tested; where each of the plurality of antenna pairs includes a transmitting antenna and a receiving antenna; and obtaining, by a vector network analyzer, the microwave signal of the brain of the subject to be tested via the antenna pairs.

In an embodiment, before filtering the microwave signal by using the MCKD to obtain the filtered signal, the method may further include:

converting the microwave signal to a time-domain microwave signal by using an inverse discrete fourier transform (IDFT).

In an embodiment, before filtering the microwave signal by using the MCKD to obtain the filtered signal, the method may further include:

determining a filter length and an impulse signal period used in the MCKD by using a particle swarm optimization.

In an embodiment, before performing the mode decomposition on the filtered signal by using the CEEMDAN to obtain the target response signal, the method may further include:

determining a noise level of the target signal in the CEEMDAN by using a particle swarm optimization.

In an embodiment, a formula for determining pixels in the target bleeding image is:

$$I(r) = \sum_{i=1}^{N}\sum_{j=1}^{N-1}[S_{i,j}(\tau(r))]^2;$$

$$\tau(r) = (|r_i - r| + |r - r_j|)/v\Delta t;$$

Where, I(r) is a pixel at a position r in the target bleeding image, N is the number of antennas, $S_{i,j}$ is a target response signal of a microwave signal transmitted from the i-th antenna and received by the j-th antenna, τ(r) is a time delay from the position r to $r_i$ and $r_j$, $r_i$ is a position of the transmitting antenna, $r_j$ is a position of the receiving antenna, v is transmission velocity of the microwave signal in the brain of the subject to be tested, and Δt is transmission time for the microwave signal from the position r to a target point.

The present disclosure further provides a system for extracting a target signal based on maximum correlated kurtosis deconvolution (MCKD), applied to the above method for extracting the target signal based on the MCKD. The system includes a plurality of antenna pairs, a vector network analyzer, and a computer; where, the plurality of antenna pairs are connected with the vector network analyzer, and the vector network analyzer is connected with the computer;

the plurality of antenna pairs are arranged along circumference of a brain of a subject to be tested; where each of the plurality of antenna pairs includes a transmitting antenna and a receiving antenna; the transmitting antenna is an antenna for transmitting transmit signals, the receiving antenna is an antenna for receiving signals, and the antenna pairs are configured to acquire a microwave signal of the brain of the subject to be tested;

the vector network analyzer is configured to receive the microwave signal of the brain of the subject to be tested, and transmit the microwave signal of the brain of the subject to be tested to the computer; and the computer is configured to: obtain the microwave signal of the brain of the subject to be tested; filter the microwave signal by using the MCKD; perform mode decomposition on the filtered microwave signal by using a CEEMDAN; and perform image reconstruction on the decomposed microwave signal by using a delay sum beamforming to obtain a target bleeding image.

In an embodiment, the antenna may be a monopole antenna.

In an embodiment, the antenna may be a patch antenna.

In an embodiment, the antenna may be made of a flexible printed circuit board.

According to the specific embodiments provided by the present disclosure, the present disclosure has the following technical effects:

According to the method for extracting the target signal based on the MCKD of the present disclosure, the microwave signal of the brain of the subject to be tested is obtained, the target response signal is obtained by using the MCKD and CEEMDAN, and image reconstruction for a bleeding target is achieved by using the delay sum beamforming according to the target response signal. The target bleeding image may be obtained through the processing on the microwave signal of the brain of the subject to be tested, improving the speed of extracting the target signal of cerebral hemorrhage.

BRIEF DESCRIPTION OF THE DRAWINGS

In order to illustrate embodiments of the present disclosure or the technical solutions of the conventional art more clearly, the accompanying drawings used in the embodiments will be briefly described below. Apparently, the accompanying drawings described below show merely some embodiments of the present disclosure. For those of ordinary skill in the art, other drawings can be obtained from these accompanying drawings without creative efforts.

DETAILED DESCRIPTION OF THE EMBODIMENTS

The technical solutions in the embodiments of the present disclosure will be clearly and completely described below in conjunction with the accompanying drawings in the embodiments of the present disclosure. Apparently, the described embodiments are merely a part of the embodiments of the present disclosure, rather than all of the embodiments. All other embodiments obtained by the ordinary skilled in the art based on the embodiments of the present disclosure without creative efforts shall fall within the scope of the present disclosure.

The present disclosure aims to provide a method and system for extracting a target signal based on maximum correlated kurtosis deconvolution (MCKD), to improve a speed of extracting a target signal for cerebral hemorrhage. The present disclosure aims to provide a target signal extraction method and system based on maximum correlated kurtosis deconvolution, which can enhance the speed of extracting a target signal of cerebral hemorrhage. The present disclosure provides a portable microwave cerebral hemorrhage imaging system using a signal processing technology for directly extracting a signal of a bleeding point with the MCKD (mckd (x, filterSize, termlter, plotMode, T, M)) and a complete ensemble empirical mode decomposition with adaptive noise (CEEMDAN).

To make the above objectives, features, and advantages of the present disclosure clearer and more comprehensible, the present disclosure is described in further detail below in conjunction with the accompanying drawings and specific implementations.

Embodiment 1

Figure 6:
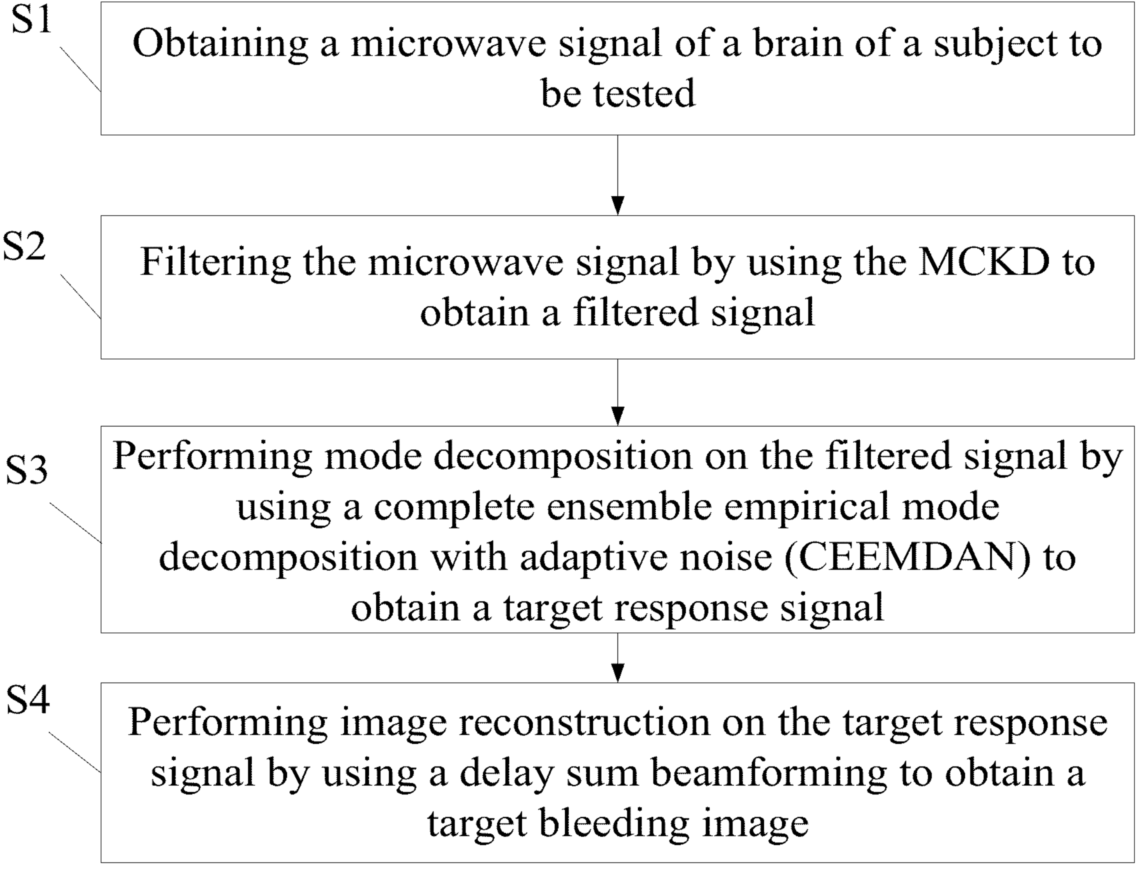
FIG. 6 is a flow chart of a method for extracting a target signal based on maximum correlated kurtosis deconvolution (MCKD)
Figure 14:
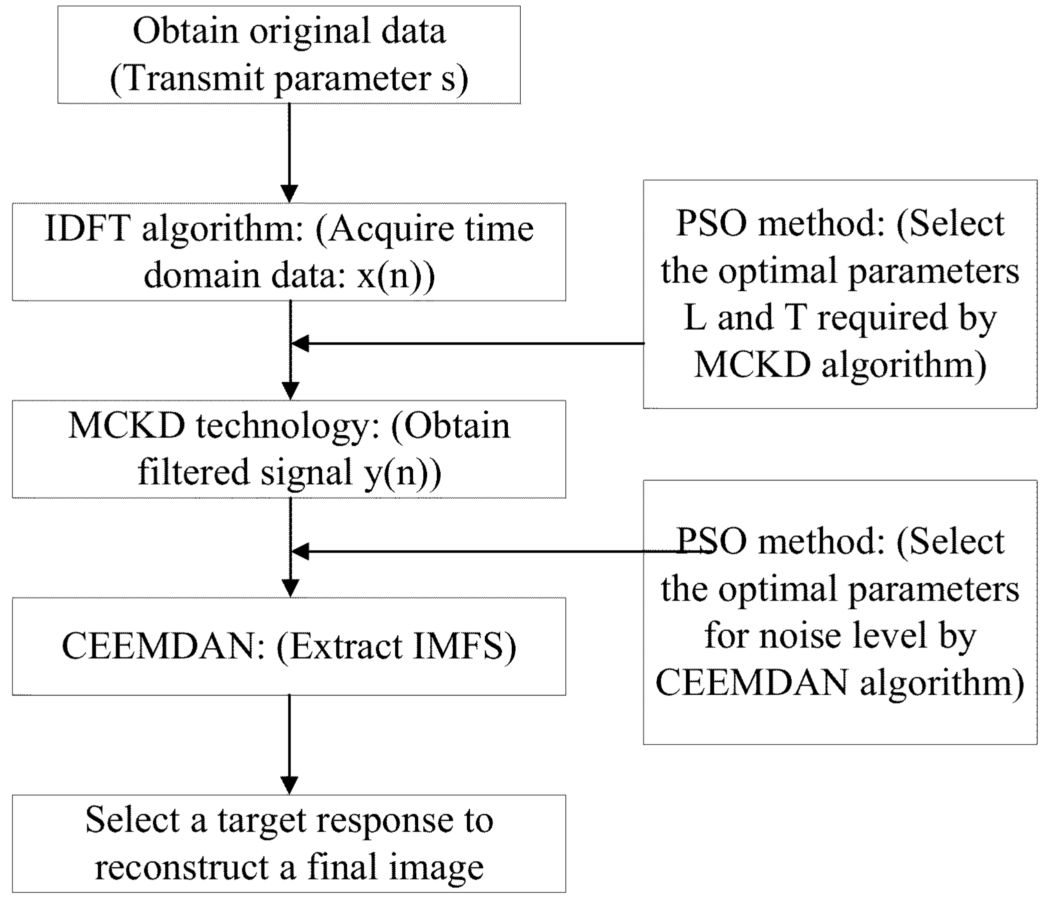
FIG. 14 is a flow chart of a method for processing a signal.

As shown in FIGS. 6 and 14, the method for extracting the target signal based on the MCKD is provided by the present disclosure, and the method includes steps S1-S4.

In step S1, a microwave signal of a brain of a subject to be tested is obtained. Specifically, a plurality of antenna pairs are arranged along circumference of the brain of the subject to be tested, where each of the plurality of antenna pairs includes a transmitting antenna and a receiving antenna; and the microwave signal of the brain of the subject to be tested is obtained by a vector network analyzer via the antenna pairs.

In step S2, the microwave signal is filtered by using the MCKD to obtain a filtered signal. Specifically, a correlation peak of the target signal is recovered from an input signal in the greatest extent by using finite impulse response (FIR) filters. An optimum filter that maximizes the correlation peak is determined by an MCKD optimization function. The microwave signal is filtered by the optimum filter to obtain the filtered signal.

In step S3, mode decomposition is performed on the filtered signal by using the CEEMDAN to obtain a target response signal. Specifically, the K-th mode, obtained by decomposing a signal subjected to white Gaussian noise processing with an Empirical Mode Decomposition (EMD), is added to the filtered signal obtained by the MCKD technology. To determine a first-order intrinsic mode function (IMF) of an original signal, a total white noise is added for N times, and results obtained after adding for N times are averaged. A residual after removing a first mode is calculated, the noise obtained by the EMD method is added to the residual to be further decomposed to obtain a second-order IMF. A residual after removing a second mode is calculated, and the above processes are repeatedly performed to obtain the remaining IMF components. Finally, the decomposition is finished when a remaining residual satisfies a monotone function condition to obtain the target response signal.

In step S4, image reconstruction is performed on the target response signal by using a delay sum beamforming to obtain a target bleeding image. Specifically, a formula for determining pixels in the target bleeding image is:

$$I(r) = \sum_{i=1}^{N} \sum_{j=1}^{N-1} [S_{i,j}(\tau(r))]^2;$$

$$\tau(r) = (|r_i - r| + |r - r_j|)/v\Delta t;$$

where, I(r) is a pixel at a position r in the target bleeding image, N is the number of antennas, $S_{i,j}$ is a target response signal of a microwave signal transmitted from the i-th antenna and received by the j-th antenna, τ(r) is a time delay from the position r to $r_i$ and $r_j$, $r_i$ is a position of the transmitting antenna, $r_j$ is a position of the receiving antenna, v is a transmission velocity of the microwave signal in the brain of the subject to be tested, and Δt is transmission time for the microwave signal from the position r to a target point.

In addition, before executing the step S2, the method may further includes:

converting the microwave signal to a time-domain microwave signal by using an inverse discrete fourier transform (IDFT); and determining a filter length and an impulse signal period used in the MCKD by using a particle swarm optimization.

Before executing step S3, the method may further include:

determining noise level of the target signal in the CEEMDAN by using the particle swarm optimization.

Embodiment 2

Figure 7:
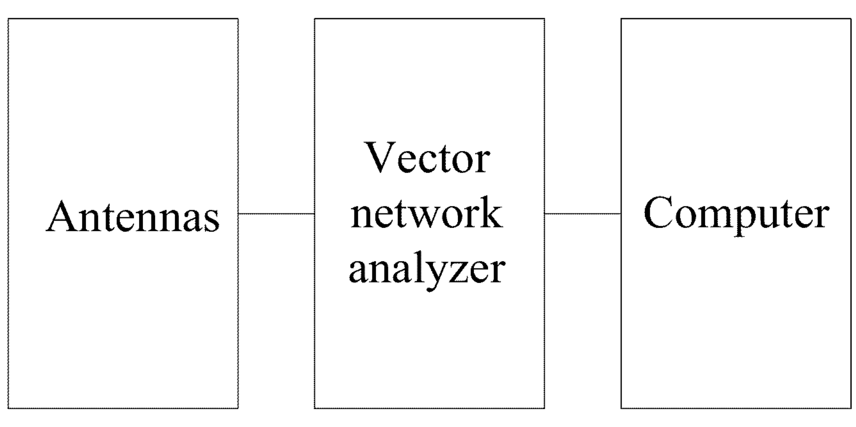
FIG. 7 is a block diagram of a system for extracting the target signal based on the MCKD.

In order to implement the method corresponding to the above embodiment 1 so as to achieve corresponding functions and technical effects, a system for extracting a target signal based on maximum correlated kurtosis deconvolution (MCKD) is provided. As shown in FIG. 7, the system includes a plurality of antenna pairs, a vector network analyzer, and a computer.

The plurality of antenna pairs are connected with the vector network analyzer, and the vector network analyzer is connected with the computer.

The plurality of antenna pairs are arranged along circumference of a brain of a subject to be tested; where each of the plurality of the antenna pairs includes a transmitting antenna and a receiving antenna; the transmitting antenna is an antenna for transmitting signals; and the receiving antenna is an antenna for receiving signals. The antenna pairs are configured to acquire a microwave signal of the brain of the subject to be tested. Specifically, the antenna is a monopole antenna and the antenna is a patch antenna.

The vector network analyzer is configured to receive the microwave signal of the brain of the subject to be tested, and transmit the microwave signal of the brain of the subject to be tested to the computer. The antenna is made of a flexible printed circuit board.

The computer is configured to: obtain the microwave signal of the brain of the subject to be tested, filter the microwave signal by using the MCKD, perform mode decomposition on the filtered microwave signal by using a CEEMDAN, and perform image reconstruction on the microwave signal obtained after mode decomposition by using a delay sum beamforming to obtain a target bleeding image.

Figure 3:
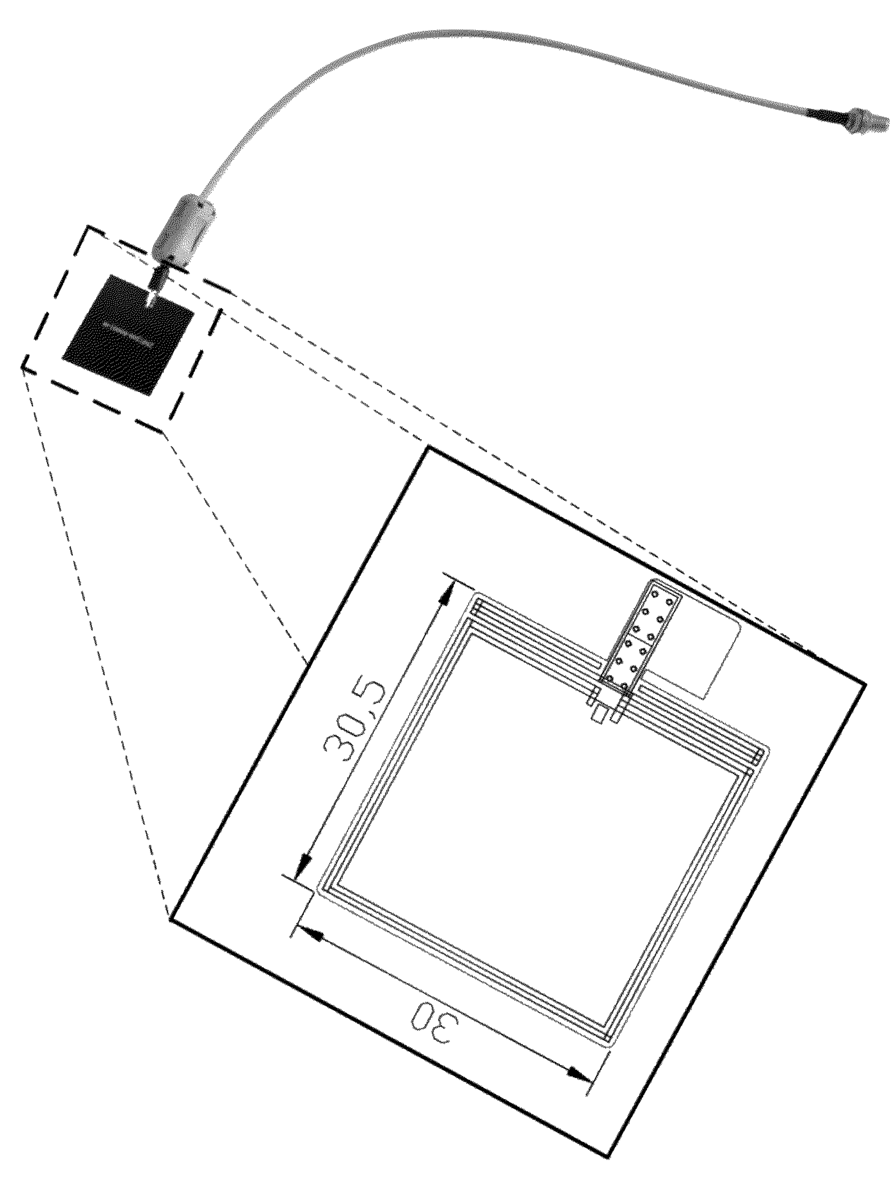
FIG. 3 is a schematic structure diagram of a real antenna.
Figure 4:
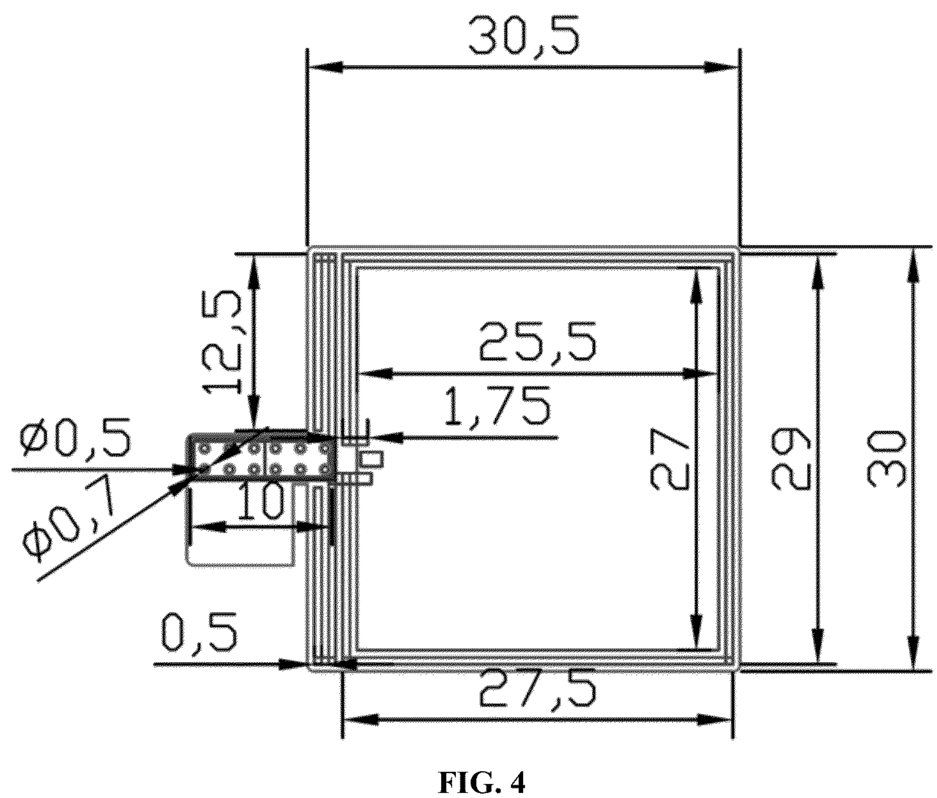
FIG. 4 is a detailed dimension drawing of a structure of the antenna.
Figure 5:
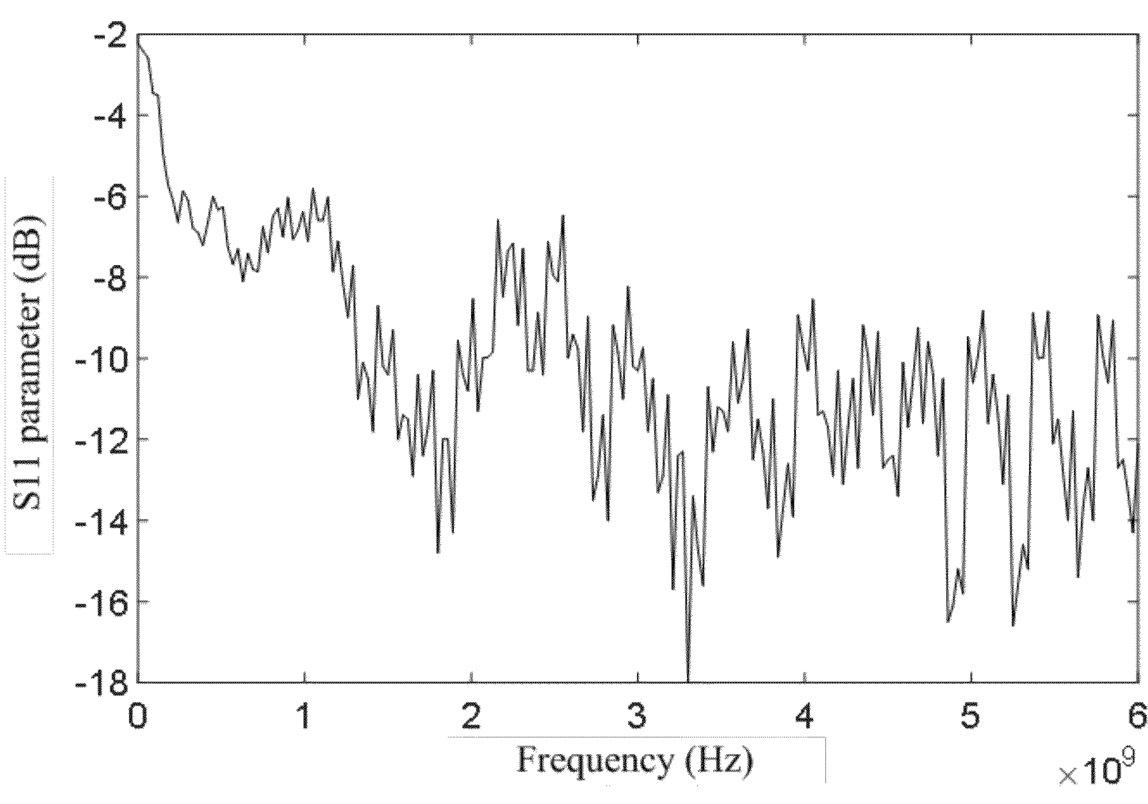
FIG. 5 is a schematic diagram of a parameter S of the real antenna tested by a vector network analyzer.
Figure 8:
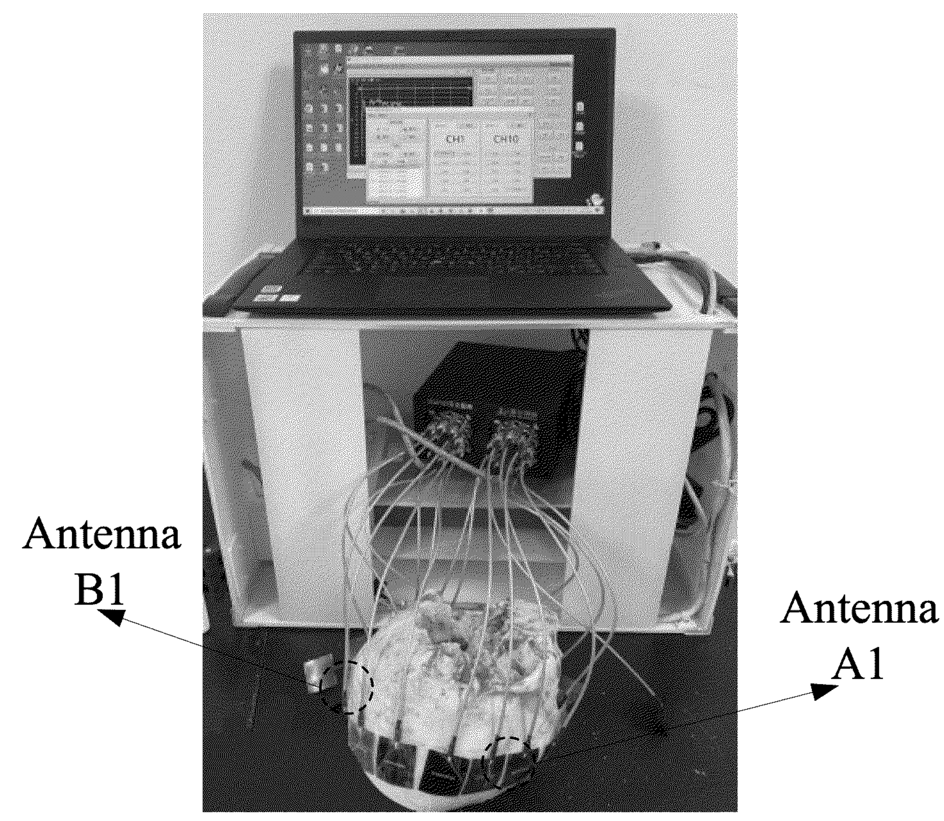
FIG. 8 is a diagram of an assembled actual measurement device.

In practical applications, a structure of an antenna is shown in FIG. 3, and detailed dimensions of the structure of the antenna in millimeters (mm) are shown in FIG. 4. The antenna has dimensions of 30 mm*30.5 mm. The basic structure of the antenna is rectangular monopole patch antenna. The folded branched long strips around the patch improve the low frequency performance of the antenna. The grounding plate of the antenna has a structure of left-right symmetry in curve strips. The antenna is made of a flexible printed circuit (FPC) board with a thickness of 0.1 mm and a dielectric constant of 3.1. A scattering parameter S of a real antenna is tested by the vector network analyzer, as shown in FIG. 5. In practical applications, the vector network analyzer in the present disclosure is Tektronix TTR506A®. The parameter of the antenna S is the scattering parameter of the antenna. A portable microwave cerebral hemorrhage imaging system is assembled as shown in FIG. 8.

Figure 15:
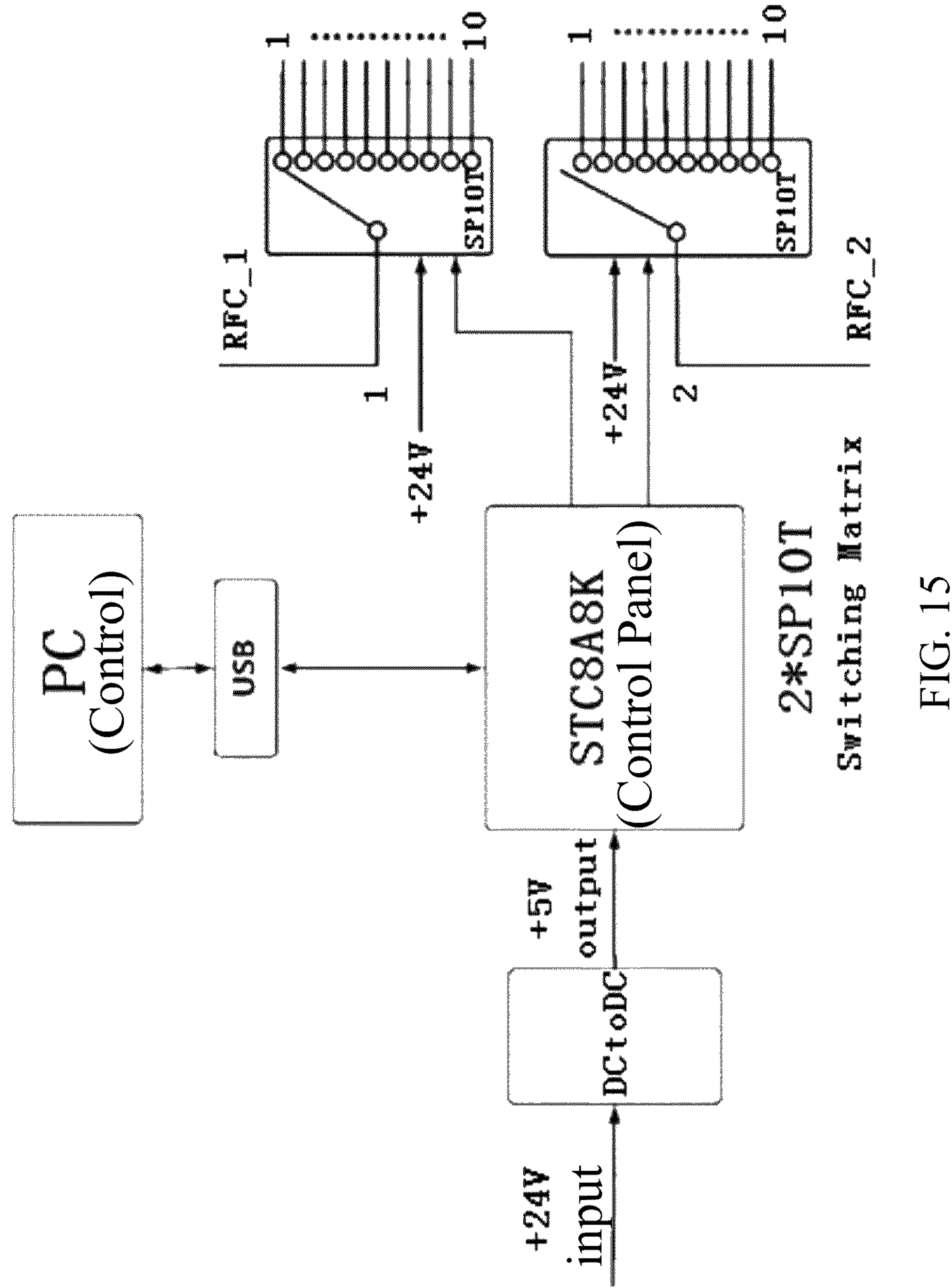
FIG. 15 is a schematic structure diagram of a circuit of a radio frequency switch.

In addition, the system for extracting the target signal based on the MCKD provided by the present disclosure further includes a 20-port radio frequency (RF) switch box. The vector network analyzer and the 20-port RF switch box are controlled by a computer to acquire original data. An antenna array consists of 14 antennas arranged along circumference of a head model. The system for extracting the target signal based on the MCKD provided by the present disclosure is portable, and the whole system has dimensions of 50 cm*41 cm*40 cm. Since the system for extracting the target signal based on the MCKD needs to arrange 14 antennas on the head of the human body, while the vector network analyzer only has two ports, a radio frequency switch is applied to solve this problem. The radio frequency switch is shown in FIG. 15. As can be seen from FIG. 15, the RF switch box consists of two SP10T RF Switches® and one STC8A8K Microcontroller®. Switching of the two RF switches is controlled by computer software via a universal serial bus (USB), which may synchronize position states of the switches. Such RF switches have a frequency range from direct current to 6 GHz.

A microwave signal is transmitted through a head model sandwiched between two patch antennas. The computer controls the vector network analyzer to receive and transmit signals, and controls the radio frequency switches to realize antenna switching. Meanwhile, the parameter S is measured and stored by the computer.

Embodiment 3

Figure 13:
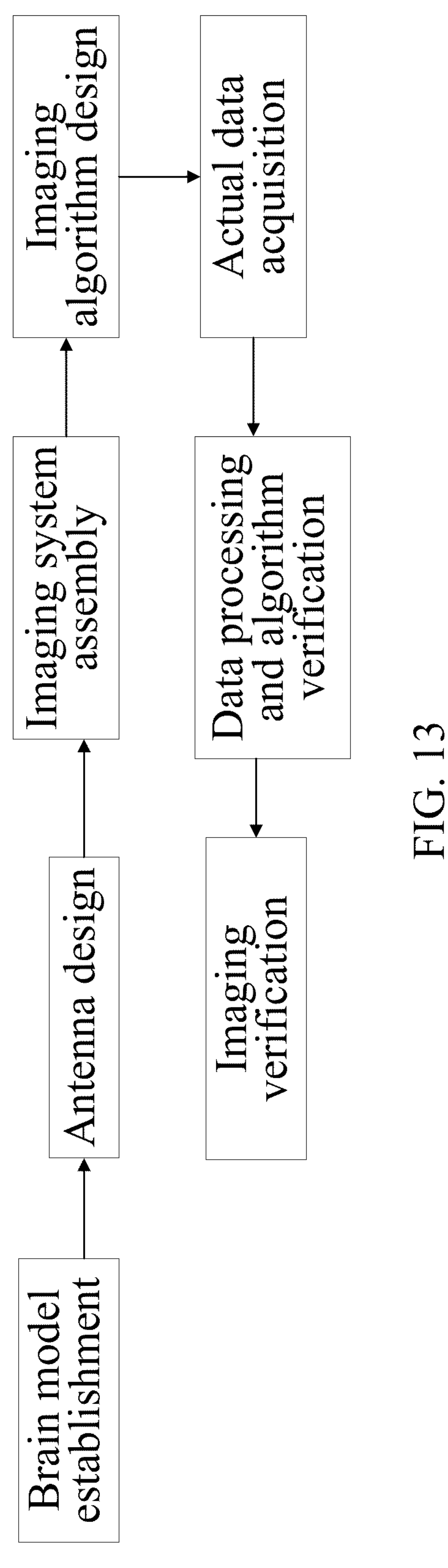
FIG. 13 is a flow chart of a research method for a portable microwave cerebral hemorrhage imaging system.

The method and system for extracting the target signal based on the MCKD will be verified below by taking a three-dimensional (3D) model of a real human brain as an example, as shown in FIG. 13.

Figure 1:
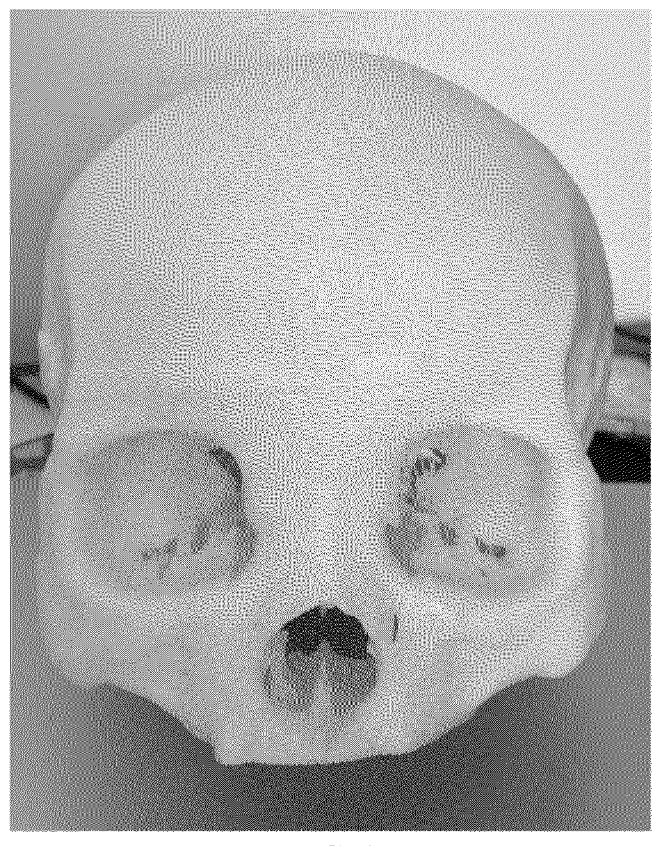
FIG. 1 is a schematic diagram of a three-dimensional (3D) model framework of a real human brain with a 3D printing according to the present disclosure.
Figure 2:
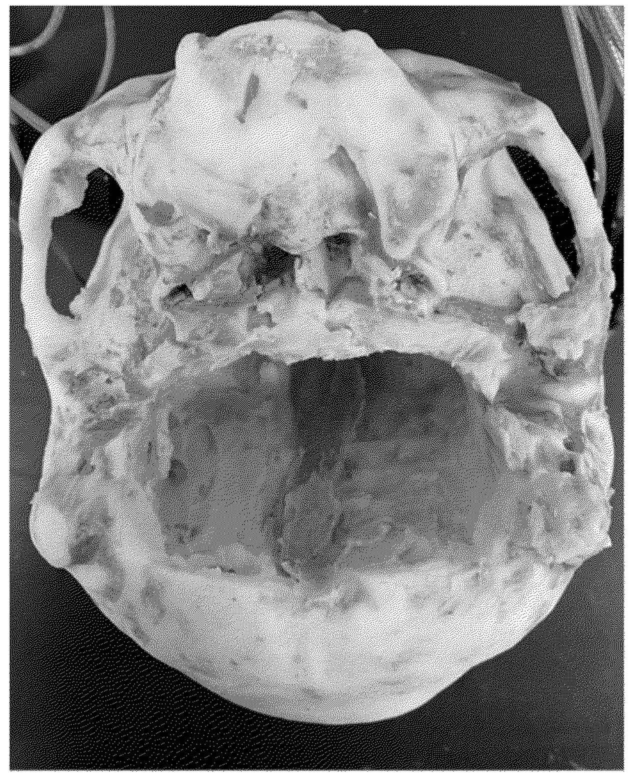
FIG. 2 is a bottom view of a whole brain model filled with brain tissue mimicking materials.

In step 101, a brain model is established. In practical applications, a magnetic resonance imaging (MRI) image of the real human brain is subjected to 3D modeling and then subjected to 3D printing. A 3D model framework of the real human brain may be obtained, as shown in FIG. 1. Relevant brain tissue mimicking materials filling the brain tissue framework are mixed. The ratios of the materials are shown in Table 1. The dielectric constant of the mimicking brain tissue is detected, and materials related to the electricity of the mimicking brain tissue are filled in the 3D model framework of the human brain shown in FIG. 1. A bottom view of a whole brain model filled with tissue mimicking materials is shown in FIG. 2.

TABLE 1

Composition Ratios of Different Tissue Mimicking Materials for the Brain Tissue

| Mimicking tissue | Deionized water (%) | Corn starch (%) | Agar (%) | Ferric chloride (%) |
|---|---|---|---|---|
| Cerebrospinal fluid | 83.05 | 2.99 | 13.87 | 0.083 |
| White matter | 64.93 | 32.13 | 2.87 | 0.068 |
| Blood | 99.21 | 0.198 | 0 | 0.595 |
| Gray matter | 65.05 | 33.09 | 1.787 | 0.071 |

In step 102, An antenna is designed. The structure of the antenna is shown in FIG. 3. Detailed dimensions of the structure of the antenna, in millimeters (mm), are shown in FIG. 4. The basic structure of the antenna is rectangular monopole patch antenna. The folded branched long strips around the patch improve the low frequency performance of the antenna. The antenna has a grounding plate with left-right symmetrical curve strips. The antenna is made of an FPC board with a thickness of 0.1 mm and a dielectric constant of 3.1. A parameter S of a real antenna is tested by a vector network analyzer.

In step 103, 14 antennas designed in step 102 are attached to the brain model designed in step 101, and the 14 antennas and a computer are connected to the vector network analyzer to finish the assembly of an imaging system.

In step 104, an imaging algorithm is designed.

The step 104 may include steps 1041-1042.

In step 1041, a microwave signal obtained in step 103 is processed by using an MCKD.

In step 10411, a correlation peak of a target signal is recovered from an input signal in the greatest extent by using FIR filters.

In step 10412, an optimum filter that maximizes the correlation peak is determined by an MCKD optimization function.

In step 1042, a mode decomposition is performed on the signal processed in the step 1041 by using a CEEMDAN.

In step 10421, the K-th mode after EMD decomposition on a signal processed by white Gaussian noise is added into a signal processed by MCKD technology.

In step 10422, the total white noise is added for N times, and the results for N times are averaged, to determine a first-order IMF of the original signal.

In step 10423, a residual after removing a first mode is calculated and added to the noise obtained by the EMD method, to be decomposed to obtain a second-order IMF.

In step 10424, a residual after removing a second mode is calculated, and the above processes are repeated to obtain the remaining IMF components. Finally, the decomposition is finished when a remaining residual satisfies a monotone function condition.

In step 105, actual data is acquired. A pair of transceiving antennas are selected for extracting a signal and performing the processing of the above step 104.

In step 106, data is processed and algorithms are verified. The step 106 may include steps 1061-1065.

Figure 9:
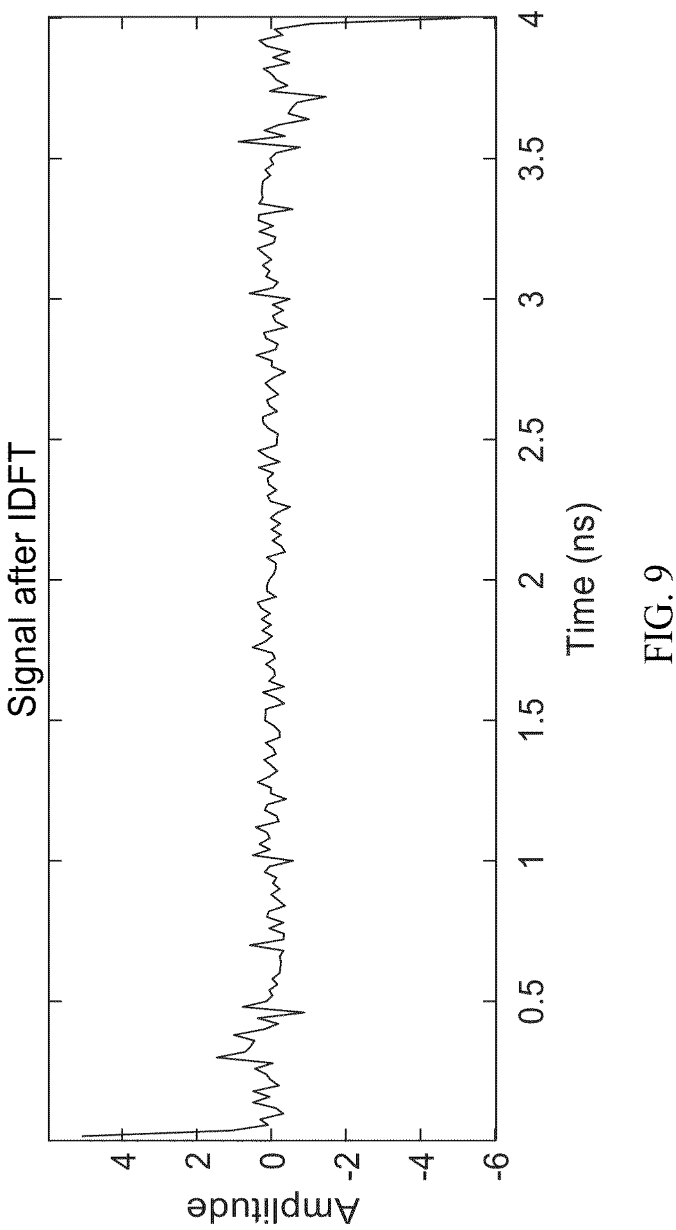
FIG. 9 is a schematic diagram of time-domain data obtained by processing a parameter S21 with an inverse discrete fourier transform (IDFT)

In step 1061, a parameter S21 is processed by using an IDFT to obtain data in time domain. The time-domain data is shown in FIG. 9.

In step 1062, a particle swarm optimization (PSO) method is adopted to help select the optimal parameters for filtering a noise signal with the MCKD technology.

Figure 10:
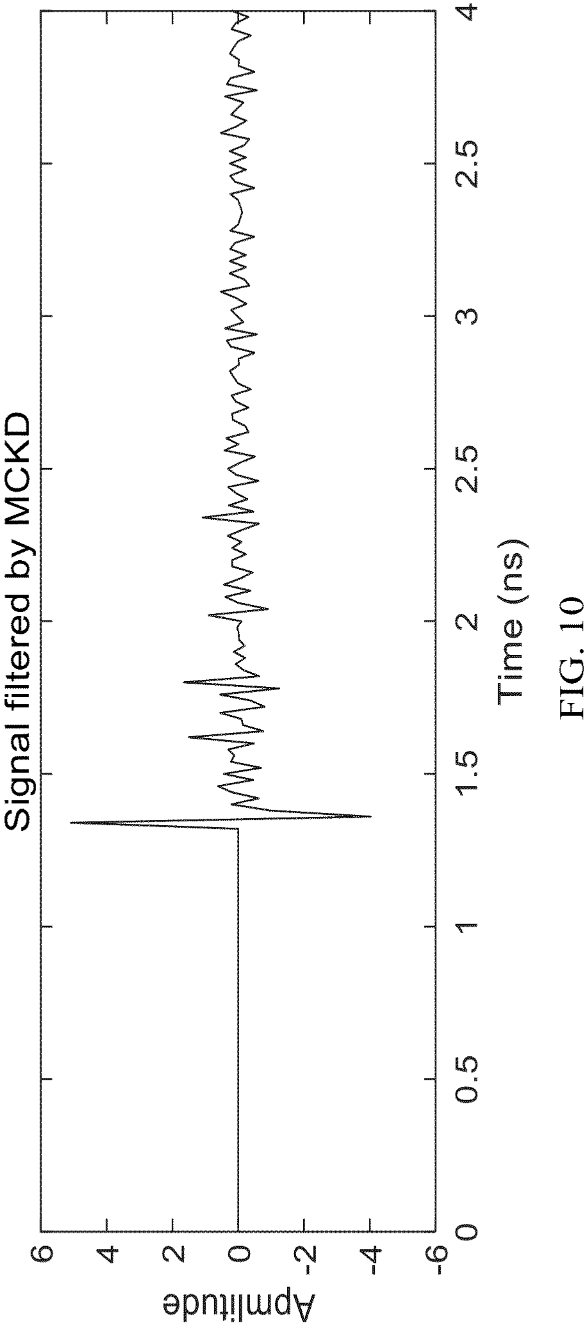
FIG. 10 is a diagram of a time-domain filtered signal.

In step 1063, the data in time domain obtained in the step 1061 is processed as in the step 1041. A pattern of the filtered time-domain signal is shown in FIG. 10.

In step 1064, the PSO method is adopted to help select the optimal parameters for performing mode decomposition on the filtered time-domain signal obtained in the step 1063 with the CEEMDAN.

Figure 11:
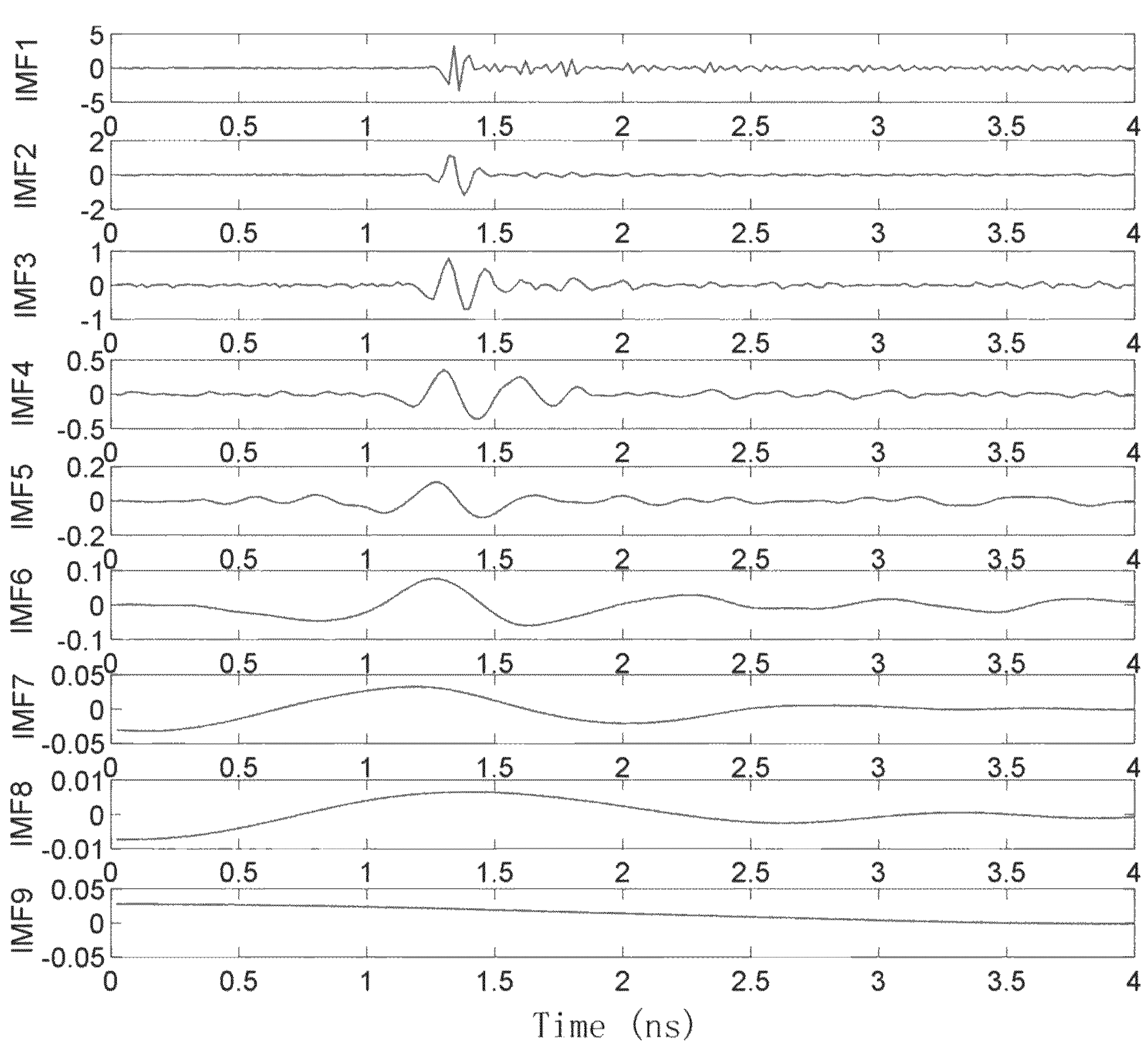
FIG. 11 is a schematic diagram of nine decomposed signals.

In step 1065, an IMF decomposition is performed on the filtered signal to obtain 9 levels of decomposed signals. FIG. 11 shows the nine signals decomposed by the algorithm. A target response may then be selected from the nine IMFs. As can be seen from FIG. 11, there are many oscillations in IMF 1 to IMF 5. IMF 6 to IMF 8 are used to reconstruct an image of a bleeding target, and only IMF 7 may provide correct information about the bleeding target. Finally, the IMF 7 is selected as a target response signal.

Figure 12:
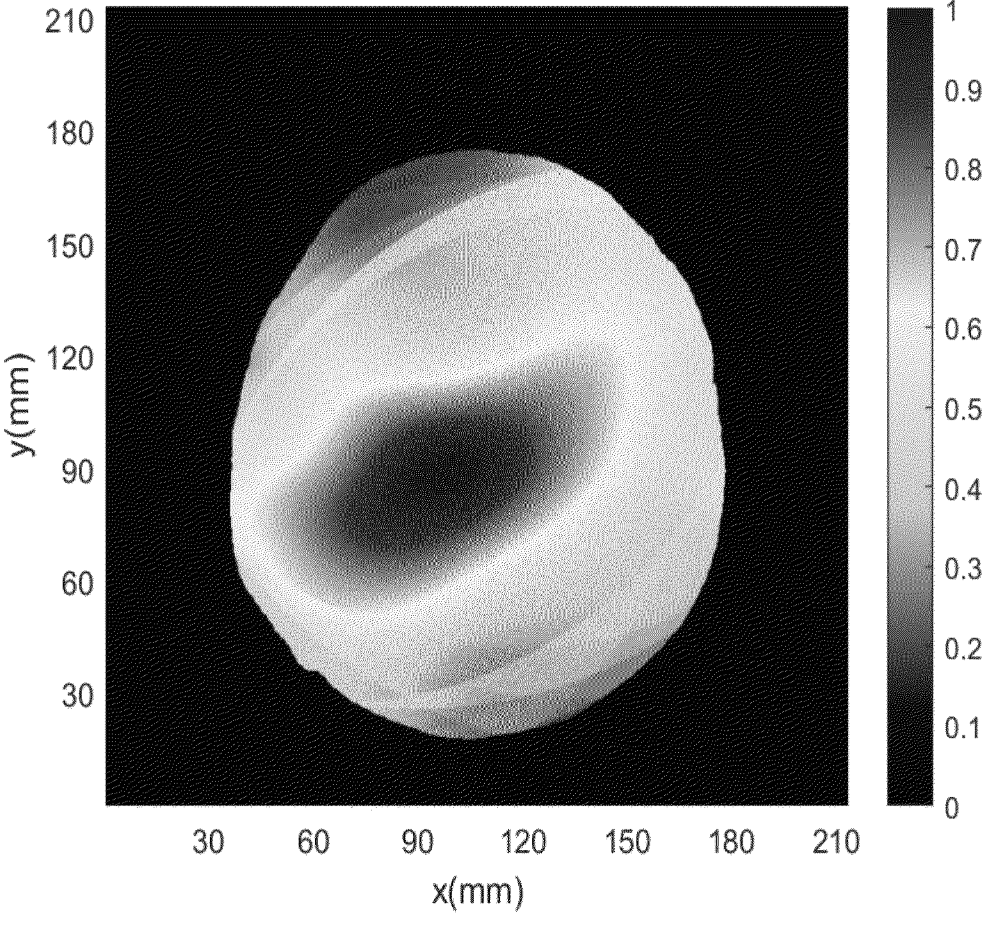
FIG. 12 is a schematic diagram of a final reconstructed image for a bleeding target.

In step 107, the imaging is verified. Specifically, after all target response signals are obtained, the image of the bleeding target is reconstructed by using a delay sum beamforming technology. FIG. 12 shows a final reconstructed image of the bleeding target obtained by processing all the IMFs 7 with the delay sum beamforming technology.

Various embodiments of the present specification are described in a progressive manner, each embodiment focuses on the difference from other embodiments, and the same and similar parts between the various embodiments may refer to each other.

In this specification, several specific examples are used for illustration of the principles and implementations of the present disclosure. The descriptions of the foregoing embodiments are used to help understand the method of the present disclosure and the core ideas thereof. In addition, for those of ordinary skill in the art, there will be changes in the specific implementations and the scope of application in accordance with the ideas of the present disclosure. In conclusion, the content of this specification shall not be construed as a limitation to the present disclosure.

What is claimed is:

1. A method for extracting a target signal based on maximum correlated kurtosis deconvolution (MCKD), comprising:

obtaining a microwave signal of a brain of a subject to be tested;

filtering the microwave signal by using the MCKD to obtain a filtered signal;

performing mode decomposition on the filtered signal by using a complete ensemble empirical mode decomposition with adaptive noise (CEEMDAN) to obtain a target response signal; and performing image reconstruction on the target response signal by using a delay sum beamforming to obtain a target bleeding image;

wherein the obtaining the microwave signal of the brain of the subject to be tested comprises:

arranging a plurality of antenna pairs along a circumference of the brain of the subject to be tested; wherein each of the plurality of antenna pairs comprises a transmitting antenna and a receiving antenna; and obtaining, by a vector network analyzer, the microwave signal of the brain of the subject to be tested via the antenna pairs.

2. The method for extracting the target signal based on the MCKD according to claim 1, before the filtering the microwave signal by using the MCKD to obtain the filtered signal, further comprising:

converting the microwave signal to a time-domain microwave signal by using an inverse discrete fourier transform (IDFT).

3. The method for extracting the target signal based on the MCKD according to claim 1, before filtering the microwave signal by using the MCKD to obtain the filtered signal, further comprising:

determining a filter length and an impulse signal period used in the MCKD by using a particle swarm optimization.

4. The method for extracting the target signal based on the MCKD according to claim 1, before performing the mode decomposition on the filtered signal by using the CEEMDAN to obtain the target response signal, further comprising:

determining a noise level of the target signal in the CEEMDAN by using a particle swarm optimization.

5. The method for extracting the target signal based on the MCKD according to claim 1, wherein a formula for determining pixels in the target bleeding image is:

$$I(r) = \sum_{i=1}^{N} \sum_{j=1}^{N-1} [S_{i,j}(\tau(r))]^2;$$

$$\tau(r) = (|r_i - r| + |r - r_j|)/v\Delta t;$$

wherein, I(r) is a pixel at a position r in the target bleeding image, N is a number of antennas, $S_{i,j}$ is a target response signal of a microwave signal transmitted from an i-th antenna and received by a j-th antenna, τ(r) is a time delay from the position r to $r_i$ and $r_i$, $r_i$ is a position of the transmitting antenna, $r_j$ is a position of the receiving antenna, vis a transmission velocity of the microwave signal in the brain of the subject to be tested, and Δt is transmission time for the microwave signal from the position r to a target point.

6. A system for extracting a target signal based on maximum correlated kurtosis deconvolution (MCKD), comprising:

a plurality of antenna pairs, a vector network analyzer, and a computer; wherein the plurality of antenna pairs are connected with the vector network analyzer, and the vector network analyzer is connected with the computer;

the plurality of antenna pairs are arranged along circumference of a brain of a subject to be tested; wherein each of the plurality of antenna pairs comprises a transmitting antenna and a receiving antenna; the transmitting antenna is an antenna for transmitting a signal, the receiving antenna is an antenna for receiving a signal, and the antenna pairs are configured to acquire a microwave signal of the brain of the subject to be tested;

the vector network analyzer is configured to receive the microwave signal of the brain of the subject to be tested, and transmit the microwave signal of the brain of the subject to be tested to the computer; and the computer is configured to:

obtain the microwave signal of the brain of the subject to be tested;

filter the microwave signal by using the MCKD;

perform mode decomposition on the filtered microwave signal by using a complete ensemble empirical mode decomposition with adaptive noise (CEEMDAN); and perform image reconstruction on the decomposed microwave signal by using a delay sum beamforming to obtain a target bleeding image.

7. The system for extracting the target signal based on the MCKD according to claim 6, wherein the antenna is a monopole antenna.

8. The system for extracting the target signal based on the MCKD according to claim 6, wherein the antenna is a patch antenna.

9. The system for extracting the target signal based on the MCKD according to claim 6, wherein the antenna is made of a flexible printed circuit board.

* * * * *